US010272140B2

(12) United States Patent
Yu et al.

(10) Patent No.: US 10,272,140 B2
(45) Date of Patent: Apr. 30, 2019

(54) THERMOSENSITIVE HYDROGEL COLLAGENASE FORMULATIONS

(71) Applicant: BioSpecifics Technologies Corp., Lynbrook, NY (US)

(72) Inventors: Bo Yu, Fresh Meadows, NY (US); Thomas L. Wegman, North Merrick, NY (US)

(73) Assignee: BIOSPECIFICS TECHNOLOGIES CORP., Lynbrook, NY (US)

(*) Notice: Subject to any disclaimer, the term of this patent is extended or adjusted under 35 U.S.C. 154(b) by 0 days.

(21) Appl. No.: 15/112,007

(22) PCT Filed: Jan. 14, 2015

(86) PCT No.: PCT/US2015/011296
§ 371 (c)(1),
(2) Date: Jul. 15, 2016

(87) PCT Pub. No.: WO2015/108901
PCT Pub. Date: Jul. 23, 2015

(65) Prior Publication Data
US 2016/0346367 A1    Dec. 1, 2016

Related U.S. Application Data

(60) Provisional application No. 62/063,056, filed on Oct. 13, 2014.

(30) Foreign Application Priority Data

Jan. 15, 2014 (CN) .......................... 2014 1 0018764

(51) Int. Cl.
| | | |
|---|---|---|
| A61K 8/04 | (2006.01) | |
| A61K 8/66 | (2006.01) | |
| A61K 9/00 | (2006.01) | |
| A61K 9/06 | (2006.01) | |
| C12N 9/52 | (2006.01) | |
| A61K 38/45 | (2006.01) | |
| A61K 47/18 | (2017.01) | |
| A61K 47/34 | (2017.01) | |
| A61Q 19/06 | (2006.01) | |
| A61K 38/48 | (2006.01) | |

(52) U.S. Cl.
CPC .......... *A61K 38/4886* (2013.01); *A61K 8/042* (2013.01); *A61K 8/66* (2013.01); *A61K 9/0019* (2013.01); *A61K 9/0024* (2013.01); *A61K 9/06* (2013.01); *A61K 47/18* (2013.01); *A61K 47/34* (2013.01); *A61Q 19/06* (2013.01); *C12N 9/52* (2013.01); *C12Y 304/24003* (2013.01); *A61K 2800/91* (2013.01)

(58) Field of Classification Search
None
See application file for complete search history.

(56) References Cited

U.S. PATENT DOCUMENTS

| | | |
|---|---|---|
| 3,821,364 A | 6/1974 | Chiulli et al. |
| 4,524,065 A | 6/1985 | Pinnell |
| 5,252,481 A | 10/1993 | Holjevac et al. |
| 5,830,741 A | 11/1998 | Dwulet et al. |
| 6,086,872 A | 7/2000 | Wegman |
| 2003/0022856 A1 | 1/2003 | Richardson et al. |
| 2003/0026844 A1 | 2/2003 | Lee et al. |
| 2005/0227910 A1 | 10/2005 | Yang et al. |
| 2006/0251581 A1 | 11/2006 | McIntyre et al. |
| 2007/0003541 A1 | 1/2007 | Faudoa et al. |
| 2007/0224183 A1 | 9/2007 | Sabatino et al. |
| 2009/0053276 A1 | 2/2009 | Richard |
| 2010/0021416 A1 | 1/2010 | Lichter et al. |
| 2010/0035868 A1 | 2/2010 | Jabbour |
| 2010/0086971 A1 | 4/2010 | Suppmann et al. |
| 2012/0315265 A1 | 12/2012 | Lai et al. |
| 2013/0129663 A1 | 5/2013 | Friberg et al. |
| 2013/0195828 A1 | 8/2013 | Kibbe |
| 2013/0217789 A1 | 8/2013 | Taylor et al. |
| 2013/0287759 A1 | 10/2013 | Munoz Montano |
| 2014/0271612 A1 | 9/2014 | Leppert et al. |

FOREIGN PATENT DOCUMENTS

| | | |
|---|---|---|
| CA | 2308842 A1 | 12/2000 |
| CA | 2643171 A1 | 9/2007 |
| EP | 0468411 A2 | 1/1992 |

(Continued)

OTHER PUBLICATIONS

Nguyen et al., Macromol. Biosci. 2010, vol. 10, p. 563-579.*
Taylor et al., Drug Discov Today Ther Strateg., 2012, vol. 9, No. 1, p. e41-e49.*
Cuggino et al., Relative & Functional Polymers, 2011, vol. 71, p. 440-446.*
Gill et al., Journal of Diabetes Science and Technology, 2007, vol. 1, Issue 5, p. 725-729.*
Madan et al., Indian J Pharm Sci. 2009, 71(3), p. 242-251, 14 pages of PDF.*
PCT International Search Report, issued in PCT/US2015/011296 dated Jun. 11, 2015, 3 pages.
International Preliminary Report dated Mar. 20, 2018, for corresponding application PCT/US2016/051670, 8 pages.

(Continued)

*Primary Examiner* — Kade Ariani
(74) *Attorney, Agent, or Firm* — Rothwell, Figg, Ernst & Manbeck, p.c.

(57) ABSTRACT

It is an object of the present disclosure to provide a formulation for injectable collagenase which will have extended residence time for the drug at the therapeutic targeted area for the indication being treated. It is a further object of the disclosure to provide a slow release formulation for collagenase which is compatible with the active ingredient and does not adversely affect its activity. Still a further object of the disclosure is to provide an injectable formulation for collagenase which can be effectively administered to a patient with a small size needle without exhibiting pregelation, which would interfere with the ability to deliver the required dose for treatment.

10 Claims, No Drawings

(56) References Cited

FOREIGN PATENT DOCUMENTS

| EP | 2130551 B1 | 9/2009 |
|---|---|---|
| EP | 2133415 A1 | 12/2009 |
| JP | 2002530873 A | 9/2002 |
| JP | 2011528716 A | 11/2011 |
| RU | 2180002 C2 | 2/2002 |
| WO | 0030182 A2 | 5/2000 |
| WO | 2006121968 A2 | 11/2006 |
| WO | 2007089851 A2 | 8/2007 |
| WO | 2007100675 A3 | 9/2007 |
| WO | 2010011605 A2 | 1/2010 |
| WO | 2011130537 A2 | 10/2011 |
| WO | 2012031245 A1 | 3/2012 |
| WO | 2012041512 A1 | 4/2012 |
| WO | WO 2012/041512  * | 4/2012 |
| WO | 2013059619 A1 | 4/2013 |
| WO | 2015/108901 A1 | 7/2015 |

OTHER PUBLICATIONS

Communication from European Patent Office in application serial No. EP 16770624.1 dated Apr. 20, 2018, 3 pages.
Office Action issued in U.S. Appl. No. 14/213,957 dated May 24, 2017, 102 pages.
Jeong, B. et al. 2000. Thermogelling biodegradable polymers with hydrophilic backbones: PEG-g-PLGA. Macromolecules 33: 8317-8322. specif. p. 8317, 8320.
Notice of Acceptance for Australian patent application No. 2015261743 dated Aug. 21, 2017, 3 pages.
Office Action issued in U.S. Appl. No. 14/853,245 dated Jun. 15, 2017, 29 pages.
Thomas, A. et al. 2010. The emerging role of Clostridium histolyticum collagenase in the treatment of Dupuytren disease. Therapeutics and Clinical Risk Management 6: 557-572. specif. pp. 557, 560, 561, 562, 565.
Canadian Office Action issued in CA 2,907,255 dated Dec. 23, 2015, 7 pages.
International Search Report and Written Opinion issued in PCT/US2016/051670 dated Nov. 21, 2016, 12 pages
Behera, MD, M.A., et al., "Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline," Reproductive Sciences, vol. 14, No. 8S, pp. 63-76 (Dec. 2007).
Brunengraber, MD, L.N. et al., "Injectable Clostridium Histolyticum Collagenase as a Potential Treatment for Uterine Fibroids," Reproductive Sciences, vol. 21(12), pp. 1452-1459 (2014).
Soledad, MD, J., et al., "Mechanical Signaling in Reproductive Tissues: Mechanisms and Importance," Reproductive Sciences, vol. 21(9), pp. 1093-1107 (2014).
Leppert, P.C., et al., "The Extracellular Matrix Contributes to Mechanotransduction in Uterine Fibroids," Hindawi Publishing Corporation, vol. 2014, Article ID 783289, pp. 1-12 (Jul. 3, 2014).
Norian, J.M., et al., "Characterization of tissue biomechanics and mechanical signaling in uterine leiomyoma," Matrix Biol., 31(1): 57-65, 12 pages. (Jan. 9, 2011).
Peavey, MD, M., et al., "Collagen-Binding α II integrin Expression in Human Myometrium and Fibroids Utilizing a Novel RNA in Situ Probe," Reproductive Sciences vol. 21(9) pp. 1139-1144, (2014).
Rogers, BS, R., et al., "Mechanical homeostasis is altered in uterine leiomyoma," Am. J. Obstet. Gynecol., 198(4): 474.e1-474.11, 22 pages (Apr. 2008).
Thorne, J.T., et al., "Dynamic Reciprocity Between Cells and Their Microenvironment in Reproduction," Biology of Reproduction, 92(1), Article 25, pp. 1-10, online before print Nov. 19, 2014. DOI 10.1095/biolreprod.114.121368.
Jayes, DVM, PhD, F.L., et al., "Loss of stiffness in collagen-rich uterine fibroids after digestion with purified collagenase Clostridium histolyticum," American Journal of Obstetrics & Gynecology, 1.e1, 8 pages (2016).

Leppert MD, PhD, P.C. et al., "Comparative ultrastructure of collagen fibrils in uterine lelornyornas and normal myometrium," Fertil Steril, 82(0 3), pp. 1182-1187 (Oct. 2004).
Stewart, E. A., Jan. 27, 2001, "Uterine fibroids." The Lancet 357:293-298, specif. p. 293.
Kikuchi, T. et al, 1998, Intra-articular injection of collagenase induces experimental osteoarthritis in mature rabbits. Osteoarthritis and Cartilage 6: 177-186. specif, pp. 177, 178.
Brandhorst, H. et al. 2008. The ratio between collagenase class I and class II influences the efficient islet release from the rat pancreas. Transplantation 85: 456-461. specif. pp. 456, 457.
Bonnerjea, J., et al., "Protein purification: the right step at the right time," Biotechnology, V. 4, 1986, pp. 954, 956 and 956.
Kågedal, L., et al., "Chemical, physical, and chromatographic properties of Superdex 75 prep grade and Superdex 200 prep grade gel filtration media," J. of Chromatography A, V. 537, 1991, pp. 17-32.
Office Action issued in Canadian application No. 2,643,171, dated Mar. 1, 2012; 3 pages.
International Search Report and Written Opinion in corresponding application No. PCT/US2012/029492, dated Aug. 20, 2012, 19 pages.
International Search Report and Written Opinion in corresponding application No. PCT/US2014/029448, dated Jul. 23, 2014, 10 pages.
Office Action issued in U.S. Appl. No. 14/213,957 dated Nov. 30, 2017, 36 pages.
Taylor, D., et al., "Putting the Moose on the Table: Understanding the Molecular Biology of Uterine Fibroids and Development of Non-invasion Treatment," XP055257658, 64 pages, Oct. 28, 2012.
Taylor; D., et al.; "Temperature-responsive biocompatible copolymers incorporating hyperbranched polyglycerols for adjustable functionality," Journal of Functional Biomaterials, vol. 2, pp. 173-194, XP009165596, Jan. 1, 2011.
Taylor, D., et al., "Recent scientific advances in leiomyoma (uterine fibroids) research facilitates better understanding and management," F1000Research, XP055257667; 11 pages, Jul. 6, 2015.
Extended European Search Report, issued in EP 16150076.4 dated Mar. 31, 2016, 11 pages.
Extended European Search Report, issued in EP 15 73 7686, dated Nov. 30, 2017, 6 pages.
Examination Report No. 1 in Australian application No. 2014228477 dated May 22, 2018, 3 pages.
Jayes, F. L., et al., "Treatment of Uterine Fibroids with Highly Purified Clostridal Collagenase," Fertility and Sterility, vol. 98, No. 3, p. S232, XP055127058, Oct. 24, 2012.
Taylor, D., et al., "Treatment for Uterine Fibroids: Searching for Effective Drug Therapies," Drug Discovery Today Therapeutic Strategies, vol. 9, No. 1, pp. e41-e49, 2012.
Australian First Examination Report issued in AU 2015261743 dated Aug. 22, 2016, 4 pages.
Office Action in Japanese application No. 2016-503099 dated Jan. 5, 2018, 4 pages.
Office Action in Japanese application No. 2015-245310 dated Jan. 19, 2018, 7 pages.
First Examination Report in European application No. 14721664.2 dated Jan. 15, 2018, 5 pages.
First Examination Report in European application No. 16150076.4 dated Jan. 12, 2018, 6 pages.
Examination Report dated Jun. 8, 2018, in Canadian application No. 2,907,255, 5 pages.
Japanese Office Action issued in JP 2016 547001 dated Sep. 20, 2018, with English translation, 7 pages.
Office Action in Japanese application No. 2016-503099 dated Dec. 7, 2018, 8 pages.
Office Action in Japanese application No. 2015-245310 dated Dec. 4, 2018, 9 pages.

* cited by examiner

THERMOSENSITIVE HYDROGEL COLLAGENASE FORMULATIONS

CROSS REFERENCE TO RELATED APPLICATIONS

This application is a National Phase of International Application Serial No. PCT/US2015/011296, filed Jan. 14, 2015, which claims priority of U.S. Provisional Patent Application No. 62/063,056, filed on Oct. 13, 2014 and Chinese Patent Application No. 201410018764.3, filed on Jan. 15, 2014, which are incorporated herein by reference in their entireties.

FIELD OF THE INVENTION

A sterile formulation for injectable collagenase which will have extended residence time for the drug at the therapeutic targeted area for the indication being treated, methods of use of such formulation and processes for its preparation.

BACKGROUND OF THE INVENTION

At present a collagenase consisting of a 1:1 mixture of Aux I and Aux II collagenases derived from clostridium histolyticum has been approved for use as a prescription medicine in the United States under the trademark Xiaflex® and in the European Union under the trademark Xiapex®. Current approved indications are for the treatment of adults suffering from Dupuytren contraction and for adult men who have Peyronies disease. In addition, this product is under clinical and pre-clinical investigation for a number of collagen lesion based human and veterinary applications such as frozen shoulder, human lipoma, canine lipoma, cellulite and uterine fibroids.

All of the aforesaid applications require local (lesion site) injection of the collagenase product. It is highly desirable that to achieve optimum clinical benefit that the collagenase remain at the lesion site for an extended period to allow the enzyme to work to maximum extent. However, the current commercial formulation of collagenase for injection is a solution prepared by reconstituting the lyophilized collagenase powder with buffered saline for injection. Data from a pharmacokinetic study has shown that a significant amount of collagenase in the commercial formulation is found in patient urine as early as thirty minutes post injection. This indicates that the administered collagenase may be washed away easily from the injection site at the lesion or other therapeutic targeted area. It is evident that formulations which provide longer residence time at the injection site can improve the therapeutic effect of the collagenase treatment.

BRIEF DESCRIPTION OF THE INVENTION

It is an object of the present invention to provide a formulation for injectable collagenase which will have extended residence time for the drug at the therapeutic targeted area for the indication being treated. It is a further object of the invention to provide a slow release formulation for collagenase which is compatible with the active ingredient and does not adversely affect its activity. Still a further object of the invention is to provide an injectable formulation for collagenase which can be effectively administered to a patient with a small size needle without exhibiting pregelation, which would interfere with the ability to deliver the required dose for treatment.

As used herein the term "collagenase" is meant to include one or more proteins exhibiting collagenase activity in a standard collagenase assay, preferably an Aux I and/or an Aux II collagenase derived from clostridium histolyticum, most preferably a 1:1 mixture of such Aux I and Aux II collagenases.

It has now been found and forms the basis of the present invention that a compatible, injectable formulation for providing a slow release of collagenase at the therapeutic targeted site can be prepared using specific reverse thermogeling hydrogels. Such hydrogels are fluid at room temperature but form a gel at the higher interbody temperature, which gel can entrap substantial amounts of the collagenase at the injection site in the body for extended release at the desired location.

Thermogelling hydrogels for delivery of therapeutic drugs is still a fairly new technology and there are still many problems to solve to achieve the desired objects of this invention. One problem is the injectability or syringeability problem which represents a critical issue for clinical usage. See for example, T. R. Hoare and D. S. Kohane, Polymer's 49 (2008) 1993-2007. High viscosity and premature gelation inside the needle are the two aspects of such injectability problem. It is common that the polymers solution comprising the hydrogel is viscous at a room temperature of about 24° C. The "thick" solution is a complication for the clinician who is administering the solution through a syringe. In order to improve patient acceptance of procedures involving multiple injections it is highly desired to use a small size needle in the syringe. However, when the scientific literature is reviewed it is interesting to observe that when hydrogels have been reported to have been injected into animals numerous citations indicate the use of large size syringes and needles. For example, ReGel®, a triblock copolymer has been used to inject drugs in humans using a 23 gauge needle (Anti-cancer Drugs, 2007, vol 18, No 3).

Due to the thermoresponsive properties of the prior hydrogel compositions, gelation inside the needle can occur after penetration of the skin but prior to discharging the contents of the syringe thus plugging up the needle. Thus, in order to have acceptable injectability for a collagenase hydrogel formulation the formulation must demonstrate that: (1) the collagenase hydrogel solution can be handled comfortably with a 0.5 mL syringe fitted with a 28G½ needle at room temperature; and (2) the needle will not exhibit pregelation after the needle has penetrated through the skin for at least 30 seconds—thus allowing the content of the syringe to be administered under normal conditions of treatment with collagenase for injection.

It is desired that the in situ gelation of the thermosensitive hydrogel/collagenase formulation at the therapeutic targeted site will entrap at least about 70 wt % of the amount of the collegenase originally contained in the original solution in the syringe and most preferably at least 80 wt % of such collagenase. The amount of collagenase in an injectable dose for present approved indications is about 0.58 mg, although the formulation can be adapted to contain more or less collagenase for other indications which may be approved in the future. The non-entrapped portion of the administered o collagenase is available for immediate treatment of the target collagen lesion while the entrapped collagenase will be released over a period of time to allow for extended treatment from the single injection. Unlike conventional gel formulations for extended release of systemic therapeutic drugs which can have release times of several weeks or even months, the release period for the collagenase gels should not exceed a few days, preferable about two days from the time of injection. Such a regime may reduce the number of injections needed for effective treatment of the lesion with minimum risk of undesired side effects from exposure of normal tissue to collagenase thus resulting in a high level of patient acceptance of this modality of treatment.

DESCRIPTION OF THE PREFERRED EMBODIMENT

DETAILED DESCRIPTION OF THE INVENTION

Numerous thermosensitive hydrogels are known in the art and are commercially available. A preferred thermosensitive hydrogel for use in the formulation of the present invention is a triblock polymer of the structure PLGA-PEG-PLGA where PLGA represents poly (DL-lactic acid-co-glycolic acid) and PEG represents poly (ethylene glycol). A commercially available triblock polymer of these materials which has (Mn=1600-1500-1600) is obtainable from Daigang Bio of Jinan, China as well as from Akina, Inc. of West Lafayette, Ind. 47906, USA.

In a further preferred embodiment of the present invention thermosensitive hydrogel materials known in the art which do not meet the requirements of injectability or compatibility due to viscosity or acidic pH can be treated in solution to modify their properties by adding to their solutions a viscosity adjusting or pH adjusting amount of the compound tris (hydroxymethyl) amino methane. In this manner such hydrogel properties will be modified to allow injection through a 28G½ needle without jamming and at a neutral or slightly basic pH, will be compatible with collagenase.

A suitable collagenase formulation for non-clinical testing can be prepared by dissolving 1 mg collagenase and 1.7 mg of a polysaccharide carrier material such as lactose in 0.5 ml of 13%-15% triblock hydrogel solution, such as PLGA-PEG-PLGA with pH adjusted to a pH 8.5 by the addition of tris (hydroxymethyl) amino methane. Such resulting solution can be readily introduced into a insulin syringe through a 28G½ needle. The basic pH has been found to be a key to having an acceptable injectability. Collagenase has been found to be stable when maintained in gels formed from the recipe when held at 37° C. for at least 48 hours. Additionally, it has been found that released and entrapped collagenase from such gels have the same biological activity as the untreated collagenase. In certain embodiments where the hydrogel exhibits a sensitivity to basic conditions it is preferred that the tris (hydroxymethyl) amino methane can be added to the hydrogel solution just prior to mixing with the collagenase powder in order to minimize any risk of degradation.

In order to provide a formulation suitable for injection the hydrogel solution has to be sterilized. Any method not involving elevated temperatures or use of materials which might affect the integrity of the hydrogel may be employed. A preferred sterilization method involves filtering the hydrogel solution through a small pore filter such as, for example, a filter with pores of about 0.22 µm into a sterile, sealable container. The resulting sterile solution can be conveniently stored prior to use as a frozen stock solution. This stock solution can be thawed when needed and used as diluent to dissolve lyophilized collagenase provided before injection.

In a further embodiment of the invention the needed components for effecting treatment of a subject for a target indication can be conveniently provided to the medical professional in kit form. Such kit would contain a sterile vial containing the thermosensitive hydrogel stock solution in an amount sufficient to provide one or more injections, one or more vials each containing a therapeutic dose for the target indication of collagenase as a lyophilized powder and optionally a package insert approved by the drug regulatory authority in the jurisdiction where the kit is to be used in treating a patient. In embodiments where the hydrogel Is sensitive to extended exposure to base conditions, It Is preferable to provide the tris (hydroxymethyl) amino methane solution In a separate vial. Most preferably the vials will be store at refrigerator or frozen conditions before use.

The preparation and use of formulations of the present invention are further illustrated by reference to the Examples which follow. It should be understood that the scope and nature of the present invention are to be defined by the claims of this application and should be not limited in any way by such Examples.

EXAMPLE 1

PLGA-PEG-PLGA—Collagenase Polymer Solution: Preparation and Characterization

Preparation of Polymer Stock Solution

A triblock polymer, poly (DL-lactic acid-co-glycolic acid)-poly (ethylene glycol)-poly(DL-lactic acid-co-glycolic acid), (PLGA-PEG-PLGA) (Mn=1600-1500-1600) was obtained from Daigang Bio., Jinan China. A 15% (w/v) polymer solution was prepared by mixing dry polymer and water at 2-8° C. The dissolution may take a few days under gentle agitation. The solution was then filtered through a 0.22 µm filter. The sterilized solution can be aliquoted and stored at −20° C. The frozen solution is preferred to be placed at refrigerator temperature overnight prior to preparing the collagenase-hydrogel solution.

Method of Polymer Dilution

The polymer solution is further diluted to 13% with water. This solution has a pH of 4. The solution is capable of forming a soft gel at 37° C. In addition to the acidic condition which causes collagenase denaturing, the 13% polymer solution was also found to be viscous at room temperature. Many published results are in fact from using chilled polymer solution, normally 4° C. A temperature of 4° C. is less than ideal as a clinical working condition which normally prefers an ambient temperature. This viscosity makes it impossible to use in a syringe. Tris buffer of pH 7.5 was then used to dilute the polymer solution. The collagenase is now safe, but the polymer solution was still too thick to be handled in a syringe at room temperature. Adjusting to pH 8.5 was found to substantially reduce the viscosity of the polymer solution at room temperature. The pH 8.5 polymer solution was a clear, fluidic solution and can be handled by a syringe with a 28G½ needle.

Preparation of Collagenase/Hydrogel Solution

Collagenase/hydrogel solution may be prepared as follows: (A) add a calculated volume of sterile 0.75 M tris buffer, pH 8.5 into a sterile polymer solution (example 1); B. add a required volume of polymer solution to lyophilized collagenase powder. The final concentration of the polymer is 13% (w/v). The dissolved collagenase is preferred to be left in a refrigerator for 30 minutes prior to injection.

EXAMPLE 2

Syringe Test at Room Temperature—Needle Test at Body Temperature

Many thermosensitive hydrogel solutions are viscous and pose a challenge for use in a syringe at room temperature :

withdrawing, expelling air etc. especially when a small size of syringe and needle is needed. A syringe test may be performed using a small size of syringe and 28G½ needle. An acceptable polymer solution should be easily handled with a small size of syringe and 28G½ needle at room temperature. The current mode of injection of collagenase solution is by intra-lesion injection, which often requires a clinician to spend time doing needle placement before pushing the plunger. Since the needle has already entered the body, gelation may occur prior to discharging the contents of the syringe. Needle test can be performed by immersing the needle into buffer warmed to 37° C. for up to 40 seconds before pushing the plunger to release the hydrogel solution.

The syringe tests demonstrate that collagenase—hydrogel solution (0.25 mL) can be handled like collagenase-saline solution. The needle tests show that the collagenase/hydrogel can be discharged easily at body temperature.

EXAMPLE 3

Sterilization Method

Polymer solutions can be sterilized by filtration at 4° C. through a 0.22 µm filter.

EXAMPLE 4

Compatibility, Initial Entrapment and Collagenase Release Test with SRC Assay Collagenase activity can be measured by a biological potency assay method—the SRC assay. This method uses soluble rat trail tendon collagen as a substrate. The assay is based on the method originally developed by Mallya (Mallya, S. K., et al. (1986) *Anal. Biochem.* 158: 334-345). The collagenase activity is measured by the amount of degraded collagen, (small peptide fragments) which is quantified by the Ninhydrin reaction. The optical density of the reaction solution (purple Ninhydrin) is measured with a spectrometer at 570 nm and compared with the ninhydrin reaction using a known amount of leucine (standard curve). The nmol peptide hydrolyzed is calculated into nmol leucine equivalent. The unit of collagenase activity was expressed as nmol leu equiv./min.

A 200 µl of collagenase/hydrogel solution was placed into a test tube with 1 mL Tris buffer (20 nM Tris(hydroxymethyl)amino methane/4 mM calcium acetate pH 7.4) prewarmed at 37° C. The gelation occurred instantly. The test tubes were incubated for various times up to 48 hr. The collagenase potency of supernatant and gel were measured with the SRC assay. The result in Table I indicate that the collagenase is compatible with the polymer and gelation process. The results show that initially more than 80% of the collagenase is entrapped in the gel. The results also show that most of the collagenase is released from the gel in 48 hours. A SDS-PAGE test showed a similar entrapment rate and release pattern. In contrast to most slow release hydrogels, the release for the present formulation is much faster. This relative "fast" slow release is more desirable for clinical uses.

TABLE I

|  | 1 hr. | 24 hr. | 48 hr. |
| --- | --- | --- | --- |
| Collagenase in test tube | 100% | 93% | 98.1% |
| Collagenase in supernatant | 13% | 51.7% | 80% |

EXAMPLE 5

Compatibility Test with GPA Assay

The hydrogel's compatibility is also verified with the second biological potency assay—GPA assay, a synthetic peptide substrate based assay. Carbobenzoxy-glycyl-L-prolyl-glycyl-glycyl-L-prolyl-L-alanine (zGPGGPA) is a synthetic substrate for Clostridial collagenase. This substrate is readily cleaved by Aux II collagenases (collagenase ABC II) into the two peptides; carbobenzolxy-glycyl-L-prolyl-glycine (zGPG) and glycyl-L-prolyl-L-alanine (GPA). The released free amino group on GPA is reacted with ninhydrin reagent. The optical density of purple ninhydrin reaction solution is measured with a spectrometer at 570 nm and compared with the ninhydrin reaction from to collagenase reference standard. The unit of collagenase activity was expressed as nmol leu equiv./min. This assay procedure was originally developed by W. Appel [in H. U. Bergmeyer, ed., Methods of Enzymatic Analysis; New York: Academic Press/Verlag Chemie, 1974].

A total of 0.353 mg of collagenase was mixed with 0.3 mL 13/2% triblock hydrogel solution, pH 8.5. 0.2 mL collagenase hydrogel solution was added to 1 mL 37° C. tris buffer in a test tube. The gelation occurred instantly. The test tube was placed on a rocker for 1 hr. at 37° C. The collagenases which went through the gelation process was compared with a control collagenase using the GPA assay. The results of 51473 units/mg for the control collagenases and 51182 units/mg for the collagenase in the gel indicate that the collagenases were compatible with the polymer.

The invention claimed is:

1. A sterile injectable formulation comprising: (1) a thermosensitive triblock polymer hydrogel; (2) an effective amount of a 1:1 mixture of Aux I and Aux II *Clostridium histolyticum* collagenase; and (3) an amount of tris (hydroxymethyl) amino methane to provide a pH of about 8.5, said formulation upon injection into a therapeutic target site in a subject having need of collagenase treatment provides to said site a gel capable of slow release of free, active collagenase mixture for no longer than about two days after injection, wherein said triblock polymer hydrogel is a poly (DL-lactic acid-co-glycolic acid) and poly (ethylene glycol) polymer of the structure PLGA-PEG-PLGA; and wherein said thermosensitive hydrogel entraps at least about 80% of said collagenase.

2. The sterile formulation of claim 1 which can be administered through a syringe fitted with a 28G½ needle without pregelation in the needle on injection.

3. A method for treating a subject suffering from a disease involving a collagen lesion which comprises injecting into the lesion the formulation of claim 1.

4. The method of claim 3 wherein said injection is made with a syringe fitted with a 28G½ needle without pregelation in said needle on injection.

5. The method of claim 3 wherein said disease is selected from Dupuytren's contracture, Peyronie's disease, frozen shoulder, human lipoma, canine lipoma, cellulite and uterine fibroids.

6. A kit for providing at least one therapeutic dose of the sterile injectable formulation of claim 1 through a syringe fitted with a 28G½ needle without pregelation in the needle on injection said kit comprising in a unit package at least one container containing a sterile thermosensitive hydrogel fluid of a triblock polymer having the structure PLGA-PEG-PLGA where PLGA is poly (DL-lactic acid-co- glycolic acid) and PEG is poly (ethylene glycol) and an amount of tris (hydroxymethyl) amino methane to provide a pH of about 8.5 in an amount sufficient for at least one therapeutic dose; at least one second container containing an effective amount of a 1:1 mixture of Aux I and Aux II *Clostridium histolyticum* collagenases in lyophilized, powder form and a package insert, wherein the formulation provides a gel capable of slow release of free, active collagenase mixture for no longer than about two days after injection.

7. The kit of claim 6 wherein the kit is maintained in a frozen form during storage.

8. A process for the preparation of the sterile injectable formulation of claim 1, said process comprising:
   (1) providing a thermosensitive hydrogel solution by mixing an amount of a triblock polymer having the structure PLGA-PEG-PLGA where PLGA is poly (DL-lactic acid-co- glycolic acid) and PEG is poly (ethylene glycol) with water and adding a sufficient amount of tris (hydroxymethyl) amino methane to said solution to provide a pH of about 8.5 (2) sterilizing said resulting solution from step (1); and (3) mixing said sterilized solution from step (2) with a therapeutically effective dose of a 1:1 mixture of Aux I and Aux II *Clostridium histolyticum* collagenase, thereby providing said sterile injectable formulation of claim 1.

9. The process of claim 8 wherein said sterilizing step is accomplished by filtering the solution from step (1) through a 0.22 µm filter.

10. The process of claim 8 wherein said tris (hydroxymethyl) amino methane solution is added to the hydrogel solution just prior to injection and is sterile.

* * * * *